(12) United States Patent
Madden et al.

(10) Patent No.: US 10,300,287 B2
(45) Date of Patent: May 28, 2019

(54) DELIVERY SYSTEMS FOR IMPLANTABLE MEDICAL DEVICES, AND ASSOCIATED TETHERING ASSEMBLIES AND METHODS

(71) Applicant: Medtronic, Inc., Minneapolis, MN (US)

(72) Inventors: Jeffrey Madden, Galway (IE); Tomas K Kelly, Galway (IE); John Gallagher, Galway (IE); Gwenda Francis, Galway (IE); Brendan Patrick Geraghty, Galway (IE); Francis Denis McEvoy, Laois (IE); Barry O'Connell, Galway (IE); Rónán Wood, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 292 days.

(21) Appl. No.: 15/193,577

(22) Filed: Jun. 27, 2016

(65) Prior Publication Data

US 2017/0368338 A1    Dec. 28, 2017

(51) Int. Cl.
*A61B 17/34*     (2006.01)
*A61N 1/362*     (2006.01)
(Continued)

(52) U.S. Cl.
CPC .......... *A61N 1/362* (2013.01); *A61B 17/3468* (2013.01); *A61N 1/3756* (2013.01); *A61N 1/37205* (2013.01); *A61N 1/37518* (2017.08)

(58) Field of Classification Search
CPC .. A61N 1/3756; A61N 1/37205; A61N 1/362; A61N 1/0573; A61N 1/372; A61N 1/059; A61N 1/05; A61N 1/0587; A61N 1/056; A61N 1/057; A61N 1/0592; A61N 1/3624; A61N 1/36507; A61N 1/371; A61N 1/37518; A61N 2001/058; A61N 2001/0585; A61N 2001/0578;
(Continued)

(56) References Cited

U.S. PATENT DOCUMENTS 3,835,864 A    9/1974  Rasor et al.
6,638,286 B1 * 10/2003  Burbank ............ A61B 17/0469
                                                606/139
(Continued)

OTHER PUBLICATIONS

U.S. Appl. No. 14/694,083, filed Apr. 23, 2015.
(Continued)

*Primary Examiner* — Robert A Lynch
*Assistant Examiner* — Mohamed G Gabr

(57) ABSTRACT

A delivery system for an implantable medical device includes a tool and a tethering member extending side-by-side within an inner shaft thereof; the tool extends within a first lumen, being in sliding engagement therein, and includes a distal end coupling feature that protrudes from a distal end of the inner shaft; and the tethering member has a first segment extending within a second lumen, and a second segment extending from the first segment and distally from the distal end of the inner shaft to an end of the tethering member, which is configured to engage with a holding member of the device, and with which the coupling feature of the tool is configured to couple. A retainer may be joined to another end of the tethering member that protrudes from a proximal port of the system.

19 Claims, 6 Drawing Sheets

(51) Int. Cl.
*A61N 1/372* (2006.01)
*A61N 1/375* (2006.01)

(58) Field of Classification Search
CPC .............. A61B 17/3468; A61B 17/064; A61B 2017/00243; A61B 2017/22035; A61B 2017/00358; A61B 2017/0649; A61B 2017/2215; A61B 2017/00473; A61B 6/12; A61M 25/0026; A61M 25/0082; A61M 25/0074; A61M 25/0105; A61M 25/0108; A61M 2025/0681
See application file for complete search history.

(56) References Cited

U.S. PATENT DOCUMENTS

| | | | |
|---|---|---|---|
| 6,852,443 | B1 | 2/2005 | Ohlsen |
| 7,011,671 | B2 | 3/2006 | Welch |
| 7,316,708 | B2 | 1/2008 | Gordon et al. |
| 8,216,158 | B2 | 7/2012 | Johnson |
| 8,364,280 | B2 | 1/2013 | Marnfeldt et al. |
| 8,504,156 | B2 | 8/2013 | Bonner et al. |
| 8,548,605 | B2 | 10/2013 | Ollivier |
| 8,615,310 | B2 | 12/2013 | Khairkhahan et al. |
| 8,721,587 | B2 | 5/2014 | Berthiaume et al. |
| 8,781,605 | B2 | 7/2014 | Bomzin et al. |
| 8,903,513 | B2 | 12/2014 | Ollivier |
| 8,945,145 | B2 | 2/2015 | Tran et al. |
| 8,958,892 | B2 | 2/2015 | Khairkhahan et al. |
| 9,205,225 | B2 | 12/2015 | Khairkhahan et al. |
| 9,216,293 | B2 | 12/2015 | Berthiaume et al. |
| 9,238,145 | B2 | 1/2016 | Wenzel et al. |
| 2005/0004602 | A1 | 1/2005 | Hart et al. |
| 2012/0095539 | A1 | 4/2012 | Khairkhahan et al. |
| 2012/0172891 | A1 | 7/2012 | Lee |
| 2012/0172892 | A1 | 7/2012 | Grubac et al. |
| 2012/0197373 | A1* | 8/2012 | Khairkhahan ....... A61N 1/3756 607/127 |
| 2013/0103047 | A1 | 4/2013 | Steingisser et al. |
| 2013/0253347 | A1 | 9/2013 | Griswold et al. |
| 2014/0018818 | A1 | 1/2014 | Somogyi et al. |
| 2014/0172034 | A1 | 6/2014 | Bomzin et al. |
| 2014/0249543 | A1 | 9/2014 | Berthiaume et al. |
| 2014/0330219 | A1 | 11/2014 | Quint |
| 2015/0051611 | A1 | 2/2015 | Schmidt et al. |
| 2015/0051613 | A1 | 2/2015 | Schmidt et al. |
| 2015/0051615 | A1 | 2/2015 | Schmidt et al. |
| 2015/0094668 | A1 | 4/2015 | Wood et al. |
| 2015/0273212 | A1 | 10/2015 | Berthiaume et al. |
| 2016/0015968 | A1 | 1/2016 | Bonner et al. |
| 2016/0015983 | A1 | 1/2016 | Sheldon |
| 2016/0059003 | A1 | 3/2016 | Eggen et al. |
| 2016/0067446 | A1 | 3/2016 | Klenk et al. |

OTHER PUBLICATIONS

U.S. Appl. No. 14/630,832, filed Feb. 25, 2015.
PCT Notification of Transmittal of the international Search Report and the Written Opinion of the International Searching Authority, dated Nov. 3, 2017, 12 pages.

* cited by examiner

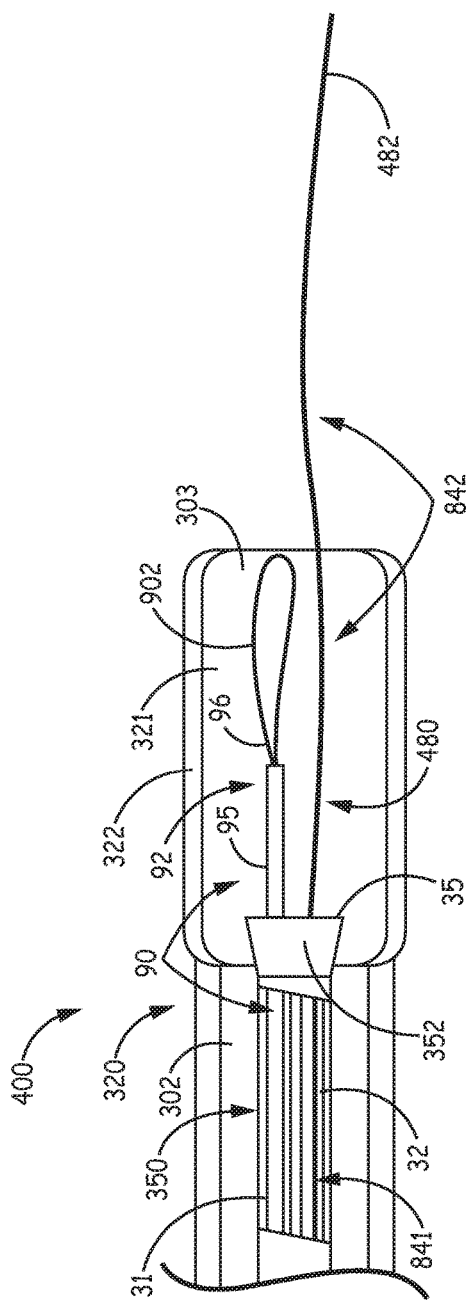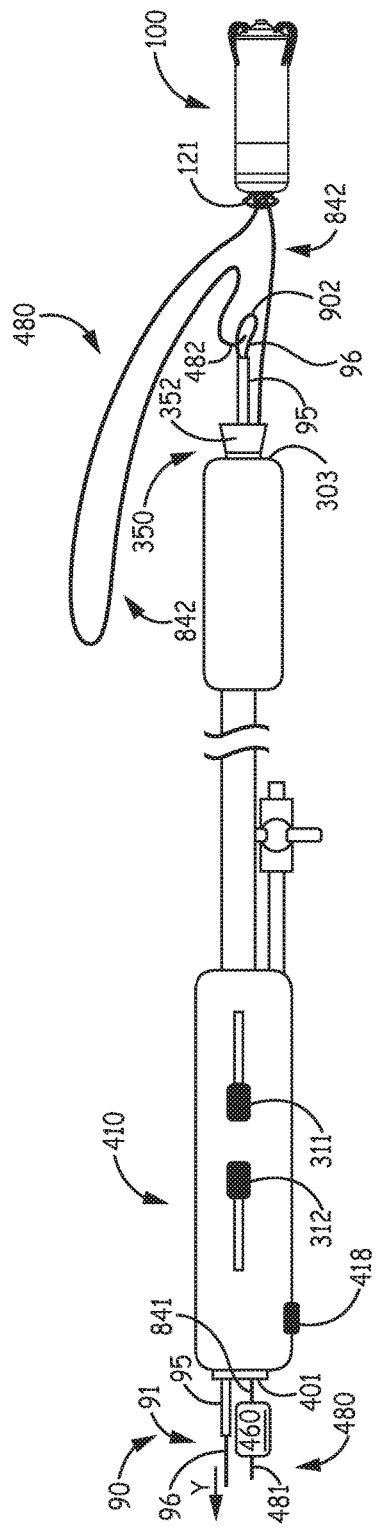
FIG. 4A
FIG. 4B

DELIVERY SYSTEMS FOR IMPLANTABLE MEDICAL DEVICES, AND ASSOCIATED TETHERING ASSEMBLIES AND METHODS

FIELD OF THE DISCLOSURE

The present disclosure pertains to delivery systems for relatively compact implantable medical devices, and more particularly to tethering of the devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed enclosure 105, preferably formed from a biocompatible and biostable metal such as titanium, contains a pulse generator, or an electronic controller and associated power source (not shown), to which at least one electrode 111 is coupled, for example, by a hermetic feedthrough assembly (not shown) like those known to those skilled in the. Enclosure 105 may be overlaid with an insulative layer, for example, medical grade polyurethane, parylene, or silicone, and a portion of the insulation layer may be removed to form another electrode 112, for example, to provide bipolar pacing and sensing in conjunction with electrode 111.

FIG. 1 shows device 100 having been deployed by an operator out from a distal opening 203 of a delivery catheter 200, which the operator has maneuvered up through the inferior vena cava IVC and the right atrium RA into the right ventricle RV. The deployed device 100 is shown fixed at an implant site by a fixation member 115 thereof, but still secured to catheter 200 by a tethering member 280 that extends out from distal opening 203 of catheter 200. After deploying device 100, the operator can grasp the ends of first and second segments 281, 282 of tethering member 280, for example, to tug on tethering member 280 to test the fixation of device 100 at the implant site, and/or to apply a greater force to tethering member 280 to remove device 100 from the implant site for repositioning at a more suitable site, if necessary. Once satisfied with the implant of device 100, the operator can separate tethering member 280 from device 100, for example, by releasing an end of tethering member first segment 281, and then pulling on an end of tethering member second segment 282 to withdraw an entirety of second segment 282 proximally through delivery catheter 200 so that first segment 281 is pulled distally and through holding member 121.

Securing device 100 to catheter 200 with tether 280 is typically accomplished by a process in which tethering member 280 is looped through device holding member 121, after which first and second segments 281, 282 of tethering member 280 are threaded through one or more lumens of catheter 200 such that opposing ends thereof protrude out from a proximal opening 201 of catheter 200. Because this process may be somewhat tedious, a manufacturer of device 100 and catheter 200 may secure the two together as a system, and provide the system to the operator in a single sterile package. However, due to shelf life considerations, the packaging of such a device separately from the associated catheter may be preferred, so that alternative means for securing/tethering the device to the catheter may be necessary to increase the ease by which an operator may load the device into the catheter at the time of an implant procedure.

SUMMARY

Embodiments and methods of the present disclosure pertain to means for tethering a relatively compact implantable medical device in a delivery system. According to some embodiments, the delivery system includes an elongate tool and an elongate tethering member extending side-by-side within an inner shaft of the system. The tool extends within a first lumen of the inner shaft, being in sliding engagement therein, and includes a distal coupling feature that protrudes from a distal end of the inner shaft; and the tethering member has a first segment extending within a second lumen of the inner shaft, and a second segment extending from the first segment and distally from the distal end of the inner shaft to an end of the tethering member, with which the coupling feature of the tool is configured to couple, wherein the end of the tethering member is configured to engage with a holding member of the device. The tethering member may also include a retainer joined to another end of the tethering member that protrudes from a proximal port of the system.

According to some methods, after engaging the second segment of the tethering member with the holding member of the device and coupling the distal end coupling feature of the tool to the engaged second segment, an operator may apply a pull force to the tool to draw the tethering member second segment into the first lumen. The pull force may be applied to the tool just until the coupled segment of the tethering member is drawn into the lumen of the system inner shaft and the device abuts the distal end of the inner shaft, after which the tool may be secured in position. According to some alternate embodiments and methods, the pull force is applied until the end of the coupled second segment protrudes from the proximal port, for example, to be joined to the tethering member retainer.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 4A is a cross-section view of a portion of a delivery system, according to some alternate embodiments;

FIG. 4B is a plan view of the system of FIG. 4A and the medical device, according to some embodiments and methods.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
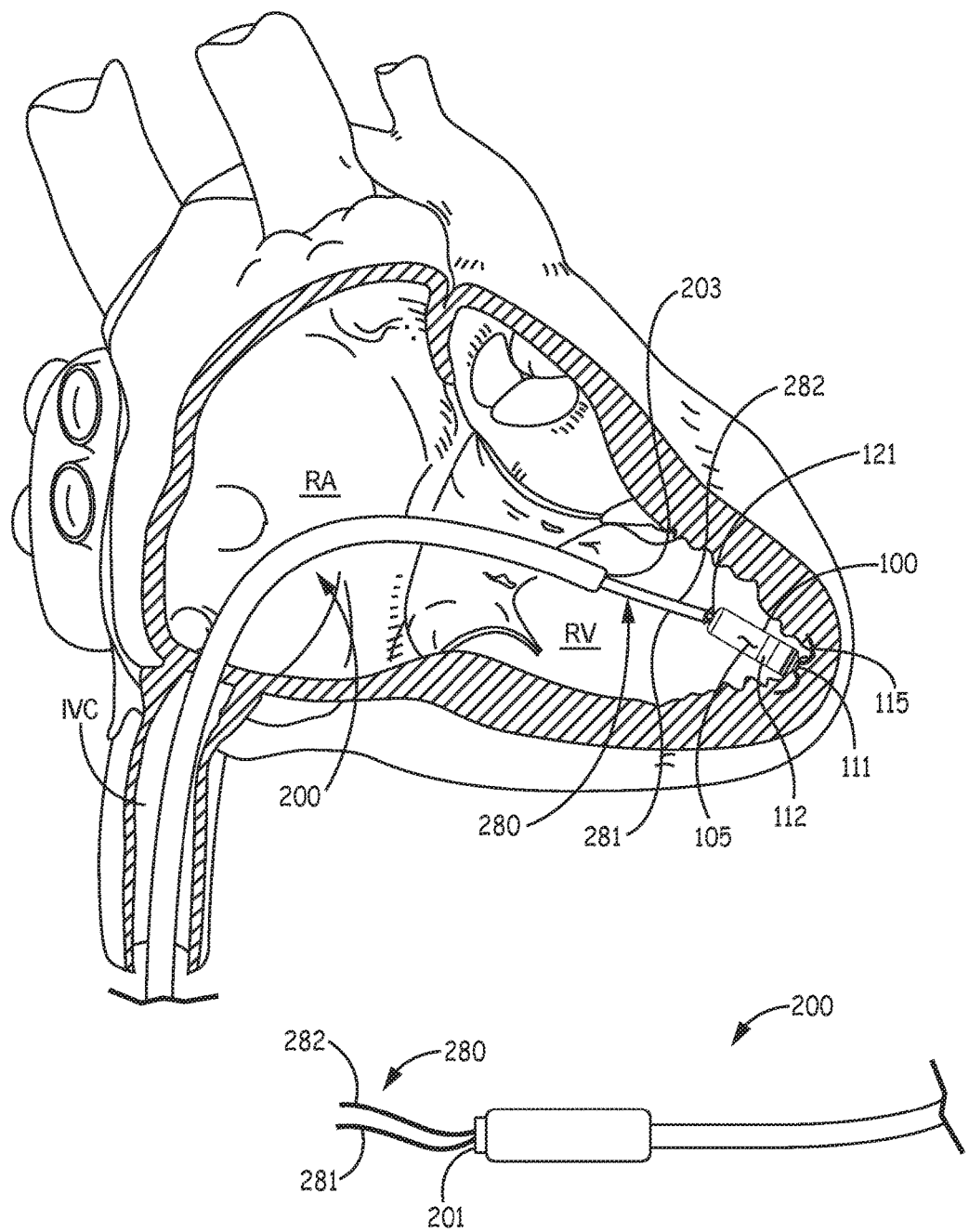
FIG. 1 is a schematic showing an exemplary implant of a relatively compact medical device, via an exemplary delivery catheter.
Figure 2:
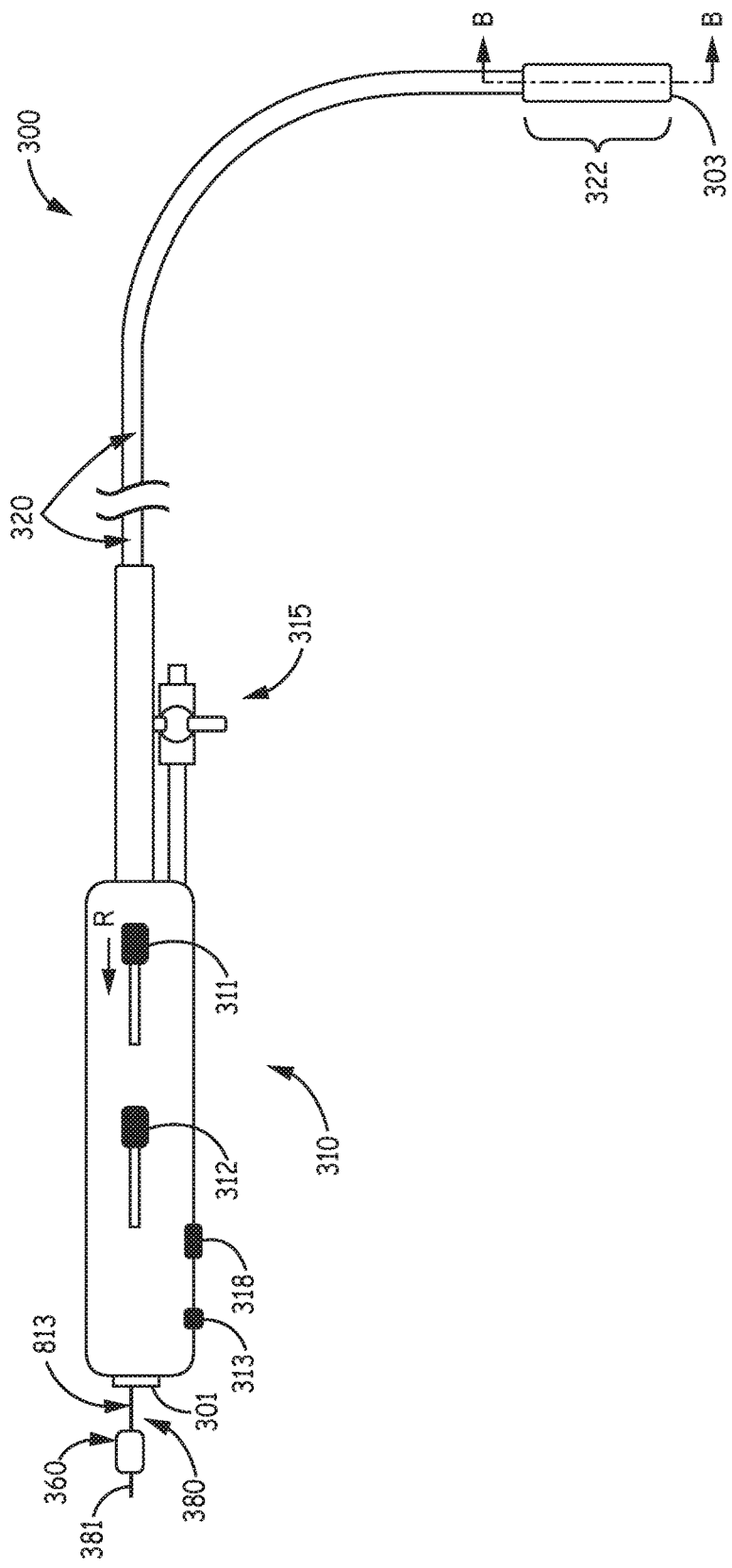
FIG. 2 is a plan view of a delivery system for a relatively compact implantable medical device, according to some embodiments.
Figure 3A:
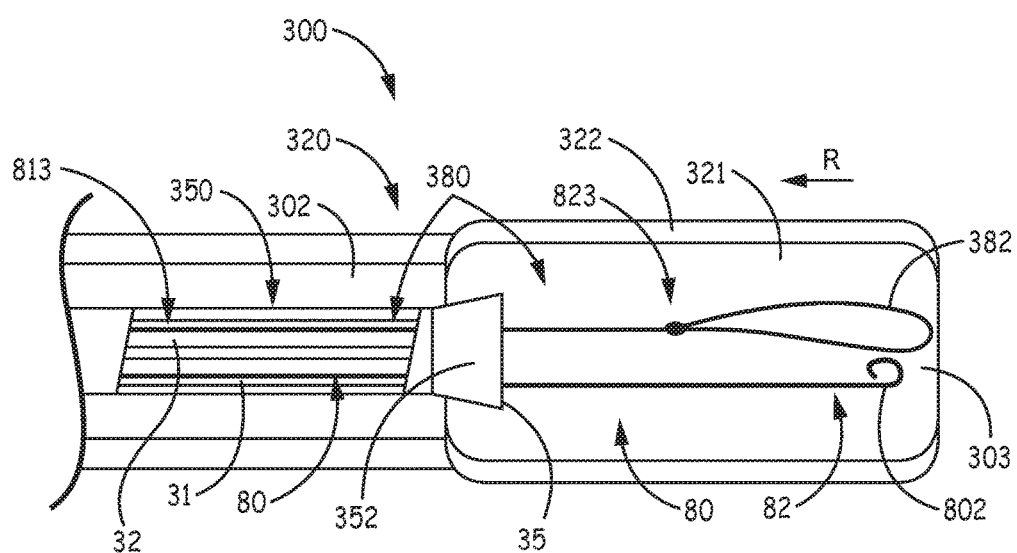
FIG. 3A is a cross-section view through section line B-B of FIG. 2, according to some embodiments.
Figure 3B:
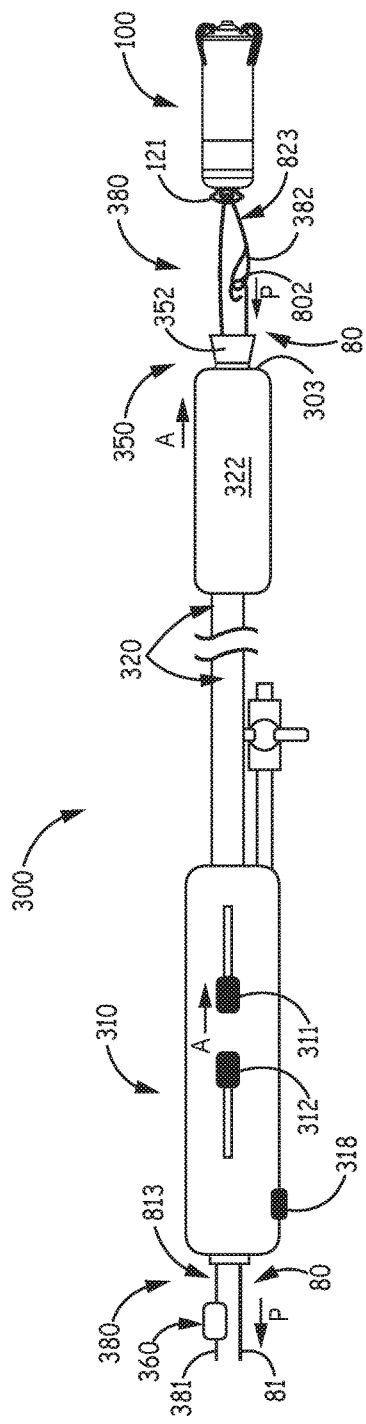
FIG. 3B is a plan view of the system of FIG. 2 and a relatively compact implantable medical device, according to some embodiments and methods.
Figure 3C:
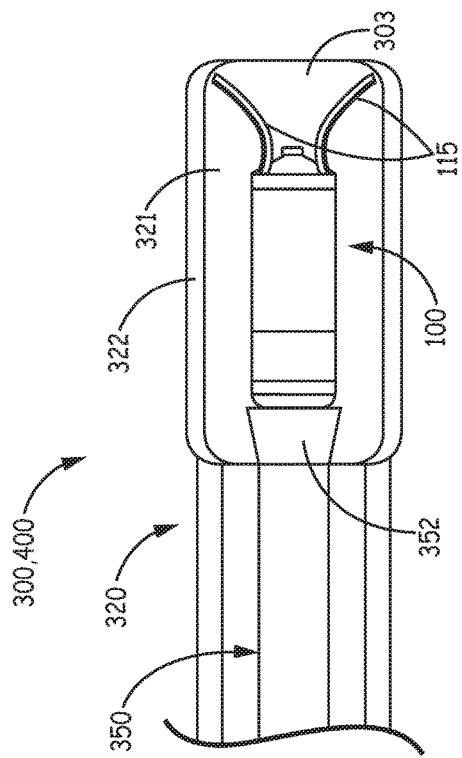
FIG. 3C is a cross-section view of the medical device tethered to the system of FIG. 2, or to the system of FIGS. 4A-C, according to some embodiments and methods.

FIG. 2 is a plan view of a delivery system 300 for a relatively compact implantable medical device, for example, device 100 described above in conjunction with FIG. 1, according to some embodiments. FIG. 2 illustrates system 300 including a handle assembly 310, an elongate outer shaft 320, and a flushing assembly 315 coupled to handle assembly 310. FIG. 2 further illustrates a distal-most portion 322 of outer shaft 320 defining a distal opening 303 of a receptacle 321 thereof (FIG. 3A), wherein receptacle 321 is sized to contain medical device 100 for delivery thereof to an implant site (FIG. 3C). According to the illustrated embodiment, outer shaft 320 is in sliding engagement around an elongate inner shaft 350, which is seen in the cross-section view of FIG. 3A (taken through section line B-B of FIG. 2). Outer shaft 320 may be coupled to a first control member 311 of handle assembly 310, which is operable to retract, per arrow R, and to advance outer shaft 320 relative to inner shaft 350. With further reference to FIGS. 2 and 3A, outer shaft 320 defines an elongate lumen 302 that is in fluid communication with receptacle 321 and flushing assembly 315.

In FIG. 3A, inner shaft 350 is shown including a first lumen 31 and a second lumen 32, each of which extend longitudinally from a proximal end of inner shaft 350 to a distal opening 35 formed at a distal end 352 of inner shaft 350. According to some embodiments, system 300 also includes a pull wire assembly, wherein a pull wire (not shown), which is coupled to a second control member 312 of handle assembly 310, extends distally from control member 312 and within a third lumen (not shown) of inner shaft 350 to an anchored distal end thereof, in proximity to inner shaft distal end 352, so that movement of second control member 312 actuates the pull wire to bend inner and outer shafts 350, 320, for example, to facilitate maneuvering delivery catheter 300 to an implant site. According to some exemplary embodiments, inner shaft 350 and outer shaft 320 may be constructed according to the description of any of the tool embodiments disclosed in the co-pending and commonly assigned United States Patent Application US 2015/ 0094668, which is hereby incorporated by reference. FIG. 3A further illustrates system 300 including an elongate tool 80 and an elongate tethering member 380, each of which extend in a corresponding lumen of first and second lumens 31, 32 of inner shaft 350 and distally out from distal opening 35. With reference back to FIG. 2, a proximal end 81 of tool 80 extends from a proximal port 301 of system 300, as does a first end 381 of tethering member 380, which is shown joined to a retainer 360, for example, a relatively hard medical grade plastic part that may be molded around first end 381.

According to the illustrated embodiment, a first segment 813 of tethering member 380 extends from first end 381 and within second lumen 32 of inner shaft 350 to a second segment 823 of tethering member 380, which extends to a second end 382 of tethering member 380. Tethering member second segment 823 is configured to engage with the aforementioned holding member 121 of device 100, for example, by being threaded through an eyelet thereof as shown in FIG. 3B; and FIG. 3A illustrates second segment 823 having a loop formed therein at second end 382 of tethering member 380, according to some embodiments. A distal end 82 of tool 80, which protrudes from inner shaft distal end 352, is shown including a coupling feature 802, which is configured, for example, in the form of a hook, to couple with second segment 823 of tethering member 380 so that a pull force applied to tool 80 is transferred to second segment 823, as described in greater detail below. Tool 80 may be formed from a medical grade stainless steel mandrel, and tethering member 380 may be formed from a polyester fiber having a fluoropolymer coating, such as PTFE.

FIG. 3B is a plan view of system 300 with tethering member second segment 823 engaged with holding member 121 of device 100. FIG. 3B illustrates coupling feature 802 of tool 80 coupled to engaged second segment 823, for example, being hooked through the loop thereof formed at tethering member second end 382. According to some methods, an operator retracts outer shaft 320 relative to inner shaft 350, as shown, before engaging tethering member second segment 823, and coupling tool coupling feature 802 to the engaged segment 823. After the engaging segment 823 with device 100, and coupling tool feature 802 to segment 823, the operator applies a pull force to proximal end 81 of tool 80, per arrow P, until tethering member second segment 823 is drawn into first lumen 31 of inner shaft 350 and device 100 abuts distal end 352 of inner shaft 350, as shown in FIG. 3C. The coupled loop of second segment 823 need only be drawn a short distance into first lumen 31 of inner shaft 350, so that tethering member second segment 823 may have a length that is significantly less than that of tethering member first segment 813. FIG. 3B further illustrates handle assembly 310 of system 300 including a locking lever 318, which the operator may activate to secure tool 80 in position, after drawing second segment 823 into lumen 31.

With further reference to FIGS. 3B-C, when device 100 abuts distal end 352 of inner shaft 350, the operator can advance outer shaft 320, per arrow A over device 100 so that a plurality of fixation fingers of fixation member 115 are moved from a relaxed condition (FIG. 3B) to an extended condition (FIG. 3C). Fixation member 115 may be cut from Nitinol tubing, according to methods known in the art, and the super-elastic nature of Nitinol allows the fingers thereof to elastically deform between the relaxed and extended conditions. The extended condition of the fixation fingers allows for initial engagement thereof with tissue at an implant site, after catheter 300 is navigated to position distal opening 303 into proximity with the implant site, and outer shaft 320 is retracted relative to inner shaft 350 and device 100. Once fixation fingers of device fixation member 115 are engaged with the tissue at the implant site, and the operator is satisfied with a performance of device 100, the operator may release locking lever 318, and cut, or otherwise detach tethering member first segment 813 from retainer 360, so that another pull force applied to tool proximal end 81 can pull first segment 813 distally through second lumen 32 of inner shaft 350, out through distal opening 35 of inner shaft 350, and out from engagement with device holding member 121.

FIG. 4A is a cross-section view of a portion of a delivery system 400, according to some alternate embodiments; and FIG. 4B is a plan view of system 400 with an elongate tethering member 480 thereof engaged with holding member 121 of device 100. System 400 includes inner and outer shafts 350, 320 like system 300, and the cross-section of FIG. 4A is comparable to that taken through section line B-B of FIG. 2. FIG. 4A illustrates an elongate tool 90 of system 400 extending in first lumen 31 of inner shaft 350, and tethering member 480 of system 400 extending in second lumen 32 of inner shaft 350. FIG. 4A further illustrates a distal end 92 of tool 90 protruding from distal end 352 of inner shaft 350; and FIG. 4B further illustrates a proximal end 91 of tool 90 protruding from proximal port 401. A first segment 841 of tethering member 480 is shown extending, within second lumen 32, to a second segment 842 of tethering member 480, which extends distally out from distal opening 35, at inner shaft distal end 352; and second segment 842 is shown being terminated by a second end 482 of tethering member 480. With reference to FIG. 4B, a first end 481 of tethering member 480, which terminates first segment 841, protrudes from a proximal port 401 of system 400 and is joined to retainer 460.

Figure 4C:
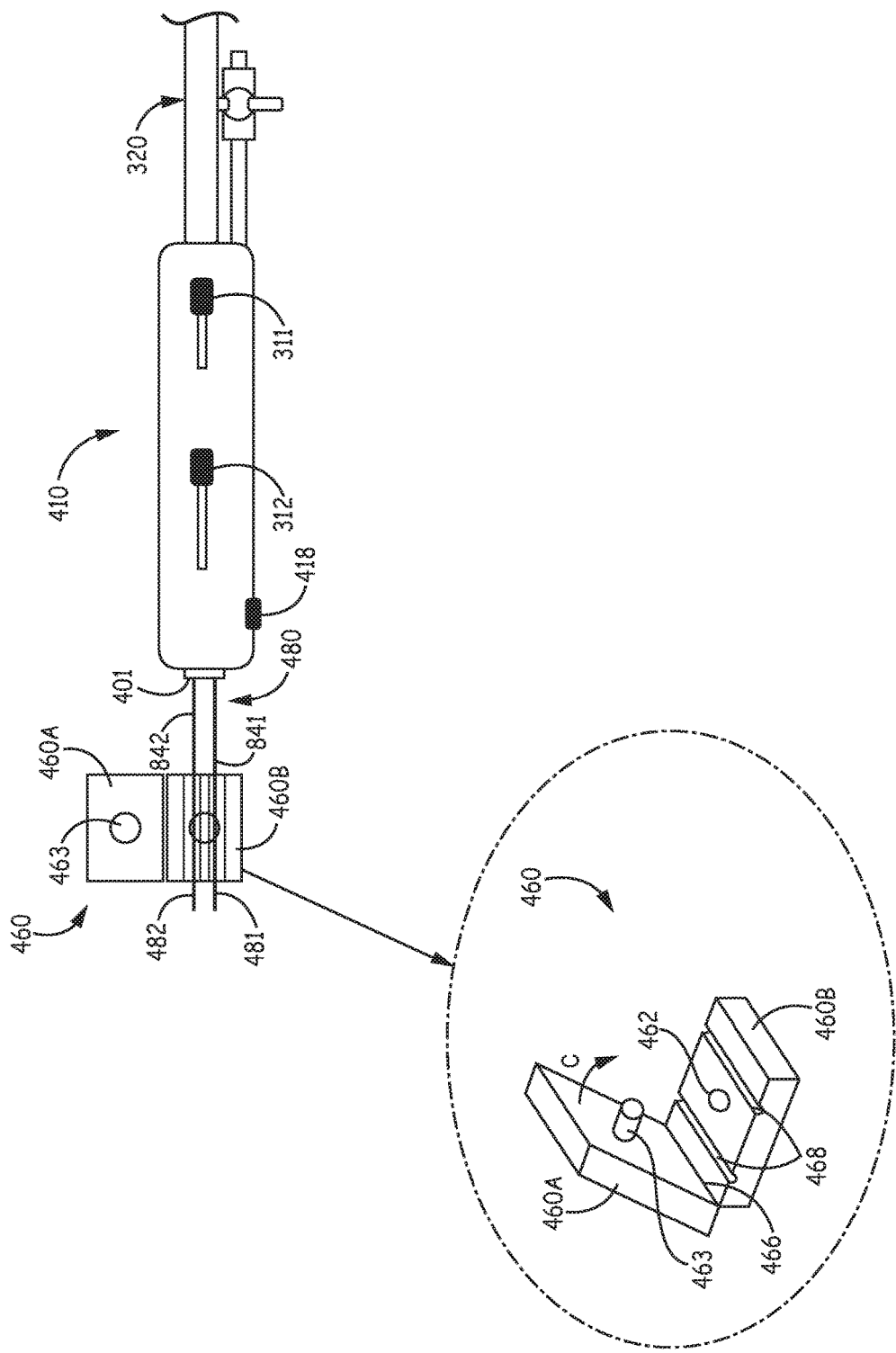
FIG. 4C is a plan view of a portion of the system of FIG. 4B along with an enlarged perspective view of a retainer that may be included in the system, according to some embodiments.

According to the illustrated embodiment, tool 90 includes an elongate tube 95 in which a snare member 96 extends in sliding engagement, wherein snare member 96 has a coupling feature 902 formed as a contractible loop at distal end 92 of tool 90 to couple with second segment 842 of tethering member 480. With reference to FIG. 4B, according to some methods, after the operator retracts outer shaft 320 relative to inner shaft 350 and engages tethering member second segment 842 with device holding member 121, for example, by threading tethering member second end 482 through the eyelet of holding member 121, the operator threads second end 482 through the loop of coupling feature 902, and then contracts the loop, by pulling snare member 96 proximally with respect to tube 95, per arrow Y, to couple engaged second segment 842 of tethering member 480 to tool distal end 92. The operator may draw coupled second segment 842 into first lumen 31 of inner shaft 350, by applying a pull force to proximal end 91 of tool 90 until second end 482 of tethering member 480 is drawn all the way through first lumen 31 and protrudes from proximal port 401 of system 400. Thus, in the illustrated embodiment of system 400, a length of tethering member second segment 842 is about the same as a length of tethering member first segment 841. After the operator uncouples tool 90 from tethering member second segment 842, the operator can secure segments 841, 842 to handle assembly 410, for example, via a locking lever 418, and then attach retainer 460 thereto, for example, as shown in FIG. 4C and described below.

FIG. 4C is a plan view of handle assembly 410 of system 400, which includes an enlarged perspective view of retainer 460 separate from system 400. FIG. 4C illustrates retainer 460 in an open position, with first and second parts 460A, 460B thereof separated from one another, to allow attachment thereto (or detachment thereof) of tethering member segments 841, 842. (It should be noted that retainer 460 may be employed in system 300 in lieu of retainer 360.) FIG. 4C further illustrates second part 460B including a pair of grooves 468, which receive first and second segments 841, 842 therein, and a receptacle 462 to receive a protrusion 463 of first part 460A in interlocking engagement therewith when retainer 460 closed, per arrow C. When the operator has positioned second segment 842 in the corresponding groove 468 of retainer 460, closing retainer 460 captures second segment 842 alongside first segment 841 in a press fit. According to an exemplary embodiment, retainer 460 is formed from any suitable medical grade plastic that has living hinge properties (e.g., Polypropylene Pro-fax™ 6523) so that first and second parts 460A, 460B may be joined together by such a hinge 466.

In the foregoing detailed description, the invention has been described with reference to specific embodiments. However, it may be appreciated that various modifications and changes can be made without departing from the scope of the invention as set forth in the appended claims.

The invention claimed is:

1. A delivery system for a relatively compact implantable medical device, the system comprising:
   an elongate inner shaft;
   an elongate outer shaft in sliding engagement around the inner shaft;
   a handle coupled to the elongate inner shaft and elongate outer shaft, the handle including a proximal port at a proximal end of the handle, the inner shaft including a first lumen and a second lumen, both lumens extending longitudinally along a length of the inner shaft from proximal openings thereof to distal openings thereof, one or both of the proximal openings being in fluid communication with the proximal port, the distal openings being located at a distal end of the inner shaft, and the outer shaft including a distal-most portion sized to contain the medical device therein;
   an elongate tool extending within the first lumen of the inner shaft and being in sliding engagement therein, the elongate tool including a proximal end accessible in proximity to the proximal port, and a distal end protruding from the distal end of the inner shaft, the distal end of the tool including a coupling feature; and
   an elongate tethering member including a first end, a second end, a first segment, a second segment, and a retainer, the first segment extending within the second lumen of the inner shaft from the first end to the second segment, the second segment extending from the first segment to the second end and distally from the distal end of the inner shaft, the first end protruding from the proximal port and being joined to the retainer proximal to the proximal port of the handle, and the second segment being configured to engage with a holding member of the medical device; and
   wherein the coupling feature of the tool is configured to couple with the second segment of the tethering member and to transfer a pull force thereto, when the pull force is applied to the proximal end of the tool, the pull force drawing the coupled second segment of the tethering member into the first lumen of the inner shaft, through the distal opening thereof.

2. The system of claim 1, wherein the second segment of the tethering member has a length that is significantly less than a length of the first segment of the tethering member.

3. The system of claim 2, wherein:
   the coupling feature of the tool comprises a hook; and
   the second segment of the tethering member has a loop formed therein at the second end.

4. The system of claim 1, wherein a length of the first segment of the tethering member is approximately equal to a length of the second segment of the tethering member.

5. The system of claim 4, wherein the retainer of the tethering member is configured for attaching to the second end of the tethering member.

6. The system of claim 5, wherein the coupling feature of the tool comprises a contractible loop configured to contract from a first loop size to a smaller second loop size.

7. The system of claim 1, wherein:
the coupling feature of the tool comprises a hook; and
the second segment of the tethering member has a loop formed therein at the second end.

8. The system of claim 1, wherein the coupling feature of the tool comprises a contractible loop configured to contract from a first loop size to a smaller second loop size.

9. The system of claim 8, wherein the contractible loop is configured to contract from the first loop size to the smaller second loop size by applying a pull force to the proximal end of the elongate tool.

10. The system of claim 1, wherein the retainer is configured to prevent the first end of the tethering member from being pulled into the second lumen.

11. The system of claim 1, wherein the coupling feature of the tool comprises a hook configured to couple with the second segment of the tethering member.

12. The system of claim 1, wherein the holding member comprises an eyelet configured to engage the second segment of the tethering member when the second segment is threaded through the eyelet.

13. A method for tethering a relatively compact implantable medical device to a delivery system, the method comprising:
engaging a second segment of an elongate tethering member of the delivery system with a holding member of the medical device, wherein the delivery system comprises:
an elongate inner shaft
an elongate outer shaft in sliding engagement around the inner shaft
a handle coupled to the elongate inner shaft and elongate outer shaft, the handle including a proximal port at a proximal end of the handle, the inner shaft including a first lumen and a second lumen, both lumens extending longitudinally along a length of the inner shaft from proximal openings thereof to distal openings thereof, one or both of the proximal openings being in fluid communication with the proximal port, the distal openings being located at a distal end of the inner shaft, and the outer shaft including a distal-most portion sized to contain the medical device therein;
an elongate tool extending within the first lumen of the inner shaft and being in sliding engagement therein, the elongate tool including a proximal end accessible in proximity to the proximal port, and a distal end protruding from the distal end of the inner shaft, the distal end of the tool including a coupling feature; and
the elongate tethering member including a first end, a second end, a first segment, the second segment, and a retainer, the first segment extending within the second lumen of the inner shaft from the first end to the second segment, the second segment extending from the first segment to the second end and distally from the distal end of the inner shaft, the first end protruding from the proximal port and being joined to the retainer proximal to the proximal port of the handle, and the second segment being configured to engage with the holding member of the medical device; and
wherein the coupling feature of the tool is configured to couple with the second segment of the tethering member and to transfer a pull force thereto, when the pull force is applied to the proximal end of the tool, the pull force drawing the coupled second segment of the tethering member into the first lumen of the inner shaft, through the distal opening thereof;
coupling the distal end of the elongate tool to the engaged second segment of the tethering member;
applying the pull force to the coupled tool until the coupled segment of the tethering member is drawn into the first lumen of the system inner shaft and the device abuts the distal end of the inner shaft; and
securing the elongate tool in position after applying the pull force.

14. The method of claim 13, further comprising retracting the outer shaft relative to the inner shaft of the system, so that the distal end of the inner shaft is exposed distal to a distal-most portion of the outer shaft, before engaging the second segment of the tethering member.

15. The method of claim 13, wherein coupling the distal end of the tool to the engaged segment of the tethering member comprises engaging a hook formed in the distal end of the tool with a loop formed in the segment of the tethering member.

16. A method for tethering a relatively compact implantable medical device to a delivery system, the method comprising:
engaging a second segment of an elongate tethering member of the delivery system with a holding member of the medical device:
an elongate inner shaft
an elongate outer shaft in sliding engagement around the inner shaft
a handle coupled to the elongate inner shaft and elongate outer shaft, the handle including a proximal port at a proximal end of the handle, the inner shaft including a first lumen and a second lumen, both lumens extending longitudinally along a length of the inner shaft from proximal openings thereof to distal openings thereof, one or both of the proximal openings being in fluid communication with the proximal port, the distal openings being located at a distal end of the inner shaft, and the outer shaft including a distal-most portion sized to contain the medical device therein;
an elongate tool extending within the first lumen of the inner shaft and being in sliding engagement therein, the elongate tool including a proximal end accessible in proximity to the proximal port, and a distal end protruding from the distal end of the inner shaft, the distal end of the tool including a coupling feature; and
the elongate tethering member including a first end, a second end, a first segment, the second segment, and a retainer, the first segment extending within the second lumen of the inner shaft from the first end to the second segment, the second segment extending from the first segment to the second end and distally from the distal end of the inner shaft, the first end protruding from the proximal port and being joined to the retainer proximal to the proximal port of the handle, and the second segment being configured to engage with the holding member of the medical device; and wherein the coupling feature of the tool is configured to couple with the second segment of the tethering member and to transfer a pull force thereto, when the pull force is applied to the proximal end of the tool, the pull force drawing the coupled second segment of the tethering member into the first lumen of the inner shaft, through the distal opening thereof;

coupling the distal end of the elongate tool to the engaged second segment of the tethering member;

applying the pull force to the coupled tool until the coupled segment of the tethering member is drawn through the first lumen of the system inner shaft and the second end of the tethering member protrudes from a proximal port of the system;

uncoupling the tool distal end from the engaged second segment of the tethering member when the second end of the tethering member protrudes from the proximal port of the system; and attaching the second end of the tethering member that protrudes from the system proximal port to the retainer of the tethering member.

17. The method of claim 16, further comprising retracting the outer shaft of the system relative to the inner shaft of the system, so that the distal end of the inner shaft is exposed distal to a distal-most portion of the outer shaft, before engaging the second segment of the tethering member.

18. The method of claim 16, coupling the distal end of the tool to the engaged second segment of the tethering member comprises passing the second segment through a contractible loop of the tool and then contracting the contractible loop.

19. The method of claim 16, wherein attaching the second end of the tethering member that protrudes from the system proximal port to the retainer comprises capturing the second end in a press fit between opposing interlocking parts of the retainer.

* * * * *